May 13, 1947. A. NAUNGAYAN Plant Pat. 736
ROSE PLANT
Filed Jan. 25, 1946
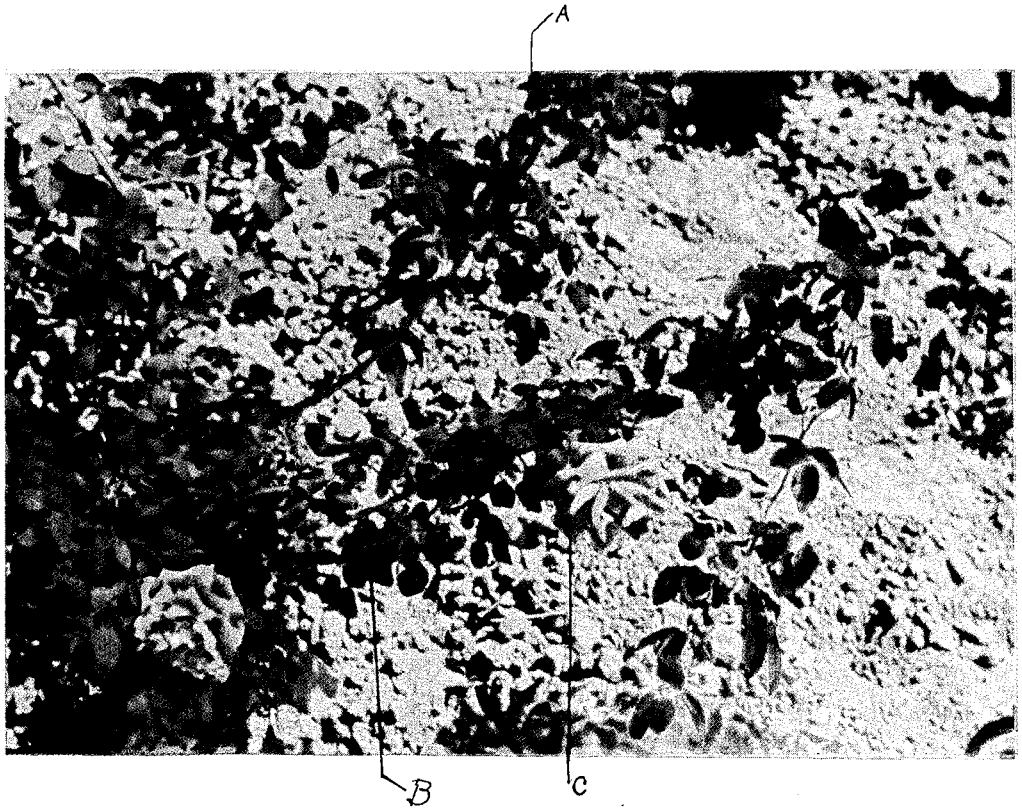
Inventor
A. Naungayan
By Robbins & Robbins
Attorneys Patented May 13, 1947

Plant Pat. 736

UNITED STATES PATENT OFFICE

736

ROSE PLANT

Antonio Naungayan, Pleasanton, Calif., assignor to Jackson & Perkins Company, Newark, N. Y., a corporation of New York Application January 25, 1946, Serial No. 643,256

1 Claim. (Cl. 47—61)

The present discovery relates to a new and distinct variety of rose plant, originating as a sport of the well-known variety "Crimson Glory" (Pl. Pat. #105) found growing by me in the nursery of Jackson & Perkins Company, at Pleasanton, California.

The dominating feature of novelty of this new rose is its climbing habit, characterized by its long, climbing shoots which bear flowers as soon as the climbing growth has stopped. As the plants grow older, the shoots grow longer.

The parent variety of this new rose is a very popular one because it is unsurpassed for its vivid, velvety crimson colored blooms, outstanding in depth of color tone. It is, however, of the low bushy type, growing vigorously to a height of only about 30".

The accompanying drawing shows a specimen of the new variety which reaches to a height of some six feet or more, increasing in height as it grows older. The long growing canes are well exemplified by this illustration at A and B, looking downwardly on the plant. The flowers, buds, and foliage are the same as the parent bush variety.

A further dominant characteristic of this new variety is its habit of sending out short auxiliary flowering branches, an example of which is shown as nearly as possible to depict at about the center of the illustration in the drawing, as at C.

Asexual reproduction of this new variety shows the foregoing characteristics come true to form and are established.

The following is a detailed description of the new variety, color terminology being in accord with Ridgway's Color Standard:

Parentage: Sport.

*Parent variety.*—"Crimson Glory."

Classification:

*Botanic and commercial.*—Climbing hybrid tea.

*Flower*

(Observations made in the fields of Jackson & Perkins Company, Newark, New York, in the morning in the month of August, 1945.)

Blooming habit: Recurrent—continuous.

Bud:

*Size.*—Large.

*Form.*—Ovoid. Is not affected by wet or hot weather.

*Color.*—When sepals first divide—Oxblood Red, Plate I. When petals begin to unfurl—Oxblood Red, Plate I. When half blown—inside of petals, between Oxblood Red, Plate I, and Carmine, Plate I, overlaid with a dark velvety sheen; reverse of petals, Oxblood Red, Plate I, suffused with Carmine, Plate I.

*Sepals.*—Slightly branched, "hood" above bud; curl back when petals begin to unfurl. Color—outside—Light Cress Green, Plate 31; inside—Light Lumiere Green, Plate 17.

*Calyx.*—Shape—funnel. Size—broad. Aspect—hairy. Color—Jade Green, Plate 31.

*Peduncle.* — Length — medium. Aspect—prickly. Color—Cress Green, Plate 31. Strength—stiff; heavy.

*Opening.*—Opens up well. Is not affected by adverse conditions.

Bloom:

*Size.*—Large. Average size when fully expanded—4½ inches to 5 inches.

*Borne.*—Singly.

*Stems.*—Medium length; strong.

*Form.*—When first open—cupped. Permanence—flattens.

*Petalage.*—Double (full but open center).

*Color.*—Center of flower—between Spectrum Red, Plate I, and Carmine, Plate I, overlaid with deep velvety sheen which disappears from the petals as the flowers open. Outer petals—between Spectrum Red, Plate I, and Carmine, Plate I, slightly overlaid with a velvety sheen. Base of petals (aiglet)—Martius Yellow, Plate III. Inside of petals—Carmine, Plate I, overlaid with a velvet sheen. Reverse of petals—Carmine, Plate I, overlaid with Amaranth Purple, Plate 12. General tonality from a distance—Carmine, Plate I.

*Discoloration.*—General tonality at end of first day—Carmine, Plate I. Second day—Carmine suffused with Spectrum Red, Plate I. Third day—Carmine suffused with Spectrum Red, Plate I.

(The velvety sheen above referred to is represented in the drawing by a heavy suffusion of Black, Plate 53.)

Petals:

*Texture.*—Leathery. Is not affected by wet or hot weather.

*Appearance.*—Inside—velvety. Outside—shiny.

*Form.*—Oval.

*Arrangement.*—Imbricated (regularly arranged shingle-like). Petaloids in center—few; small.

*Persistence.*—Drop off cleanly.

*Fragrance.*—Strong. Nature—"Old Rose perfume" (Centifolia).

*Lasting quality.*—On the plant and as cut flower—Long.

Genital organs:

*Stamens, anthers.*—Size—medium; many. Color—Buff Yellow, Plate 4. Arrangement—regular around styles.

*Stamens, filaments (threads).*—Length—short. Color—Maize Yellow, Plate 4.

*Pollen.*—Apricot Yellow, Plate 4.

*Styles.*—Bunched; even; short; heavy.

*Stigmas.*—Eugenia Red, Plate 12.

*Ovaries.*—All enclosed in calyx.

*Plant*

Form: Climber.

Growth: Vigorous.

Foliage: Five leaflets.

*Size.*—Medium.

*Quantity.*—Abundant.

*Color.*—New foliage: upper side—Parrot Green, Plate 6; serrations Oxblood Red, Plate 1; under side—Yellowish Oil Green, Plate 5, overcast with Oxblood Red, Plate 1. Old foliage: upper side—Forest Green, Plate 17; under side—Light Cress Green, Plate 31.

*Shape.*—Oval pointed.

*Texture.*—Upper side—glossy; smooth. Under side—smooth. Ribs and veins—moderately prominent.

*Edge.*—Serrated.

*Serration.*—Single; small.

*Leaf stem.*—Light Cress Green, Plate 31. Under side—prickles.

*Stipules.*—Medium length; smooth.

*Disease resistance.*—Resistant.

Wood:

*New wood*—Van Dyke Red, Plate 13. Bark—smooth.

*Old wood.*—Cress Green, Plate 31. Bark—smooth.

Thorns:

*Thorns.*—Quantity—on main stalks from base and on laterals from stalk—ordinary. Form—broad base; medium length; hooked downward. Color when young—Oxblood Red, Plate 1. Position—irregular.

*Prickles.*—Quantity—on main stalks and on laterals—few.

*Short needles.*—Quantity—on main stalks and on laterals—none.

I claim:

A new and distinct variety of rose plant characterized as to novelty by its climbing habit, and its habit of sending out short auxiliary flowering branches, substantially as shown and described.

ANTONIO NAUNGAYAN.

REFERENCES CITED

The following references are of record in the file of this patent:

UNITED STATES PATENTS

| Number | Name | Date |
|---|---|---|
| Pl. Pt. 105 | Kordes | Oct. 16, 1934 |